(12) United States Patent
Frewin et al.

(10) Patent No.: US 10,046,165 B2
(45) Date of Patent: Aug. 14, 2018

(54) MAGNETIC RESONANT IMAGING SAFE STYLUS

(71) Applicants: University of South Florida, Tampa, FL (US); George Mason University, Fairfax, VA (US)

(72) Inventors: Christopher Leroy Frewin, Tampa, FL (US); Joseph Jonathan Register, Tampa, FL (US); Stephen E. Saddow, Odessa, FL (US); Meralys Reyes-Natal, Tampa, FL (US); Joseph J. Pancrazio, Boyds, MD (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 15/303,545

(22) PCT Filed: Apr. 21, 2015

(86) PCT No.: PCT/US2015/026824
§ 371 (c)(1),
(2) Date: Oct. 12, 2016

(87) PCT Pub. No.: WO2015/164340
PCT Pub. Date: Oct. 29, 2015

(65) Prior Publication Data
US 2017/0050029 A1     Feb. 23, 2017

Related U.S. Application Data (60) Provisional application No. 61/981,940, filed on Apr. 21, 2014.

(51) Int. Cl.
*A61N 1/375*     (2006.01)
*A61B 5/00*     (2006.01)
(Continued)

(52) U.S. Cl.
CPC .......... *A61N 1/375* (2013.01); *A61B 5/04001* (2013.01); *A61B 5/055* (2013.01); *A61B 5/6868* (2013.01); *A61N 1/0534* (2013.01)

(58) Field of Classification Search
CPC combination set(s) only.
See application file for complete search history.

(56) References Cited

U.S. PATENT DOCUMENTS 7,962,224 B1     6/2011  Blischak
8,326,436 B2    12/2012  Li et al.
(Continued)

FOREIGN PATENT DOCUMENTS

EP     2599522     6/2013

OTHER PUBLICATIONS

International application No. PCT/US2015/026824 filed Apr. 21, 2015, International Search Report and the Written Opinion of the International Searching Authority dated Jul. 16, 2015.
(Continued)

*Primary Examiner* — Robin Mishler
(74) *Attorney, Agent, or Firm* — Thomas|Horstemeyer, LLP.

(57) ABSTRACT

An implantable magnetic resonant imaging (MRI) safe stylus for biomedical devices is described. In one example, the stylus includes a set of stylus modules. One or more of the stylus modules includes a core rod formed of silicon carbide (SiC) material, a recording array mounted on the core rod, and a stimulation array mounted at a distal end of the core rod. The stylus also includes a hemispherical cap formed of SiC material. In part due to the construction and choice of materials used in the stylus, it does not substantially couple with electromagnetic fields during an MRI, for example. Therefore, the stylus does not produce excessive additional heat. The designs described herein also rely on the
(Continued)

high thermal transport but low heat capacity of SiC to provide a thermal pathway which will conduct induced heat throughout the stylus, to dissipate heat more evenly.

20 Claims, 9 Drawing Sheets (51) Int. Cl.
*A61B 5/04* (2006.01)
*A61B 5/055* (2006.01)
*A61N 1/05* (2006.01)

(56) References Cited

U.S. PATENT DOCUMENTS

| | | | |
|---|---|---|---|
| 8,369,964 | B2 | 2/2013 | Ameri |
| 8,391,994 | B2 | 3/2013 | Foster et al. |
| 8,601,672 | B2 | 12/2013 | Tranchina |
| 2002/0042634 | A1* | 4/2002 | Bardy .................. A61N 1/375 607/36 |
| 2002/0143379 | A1 | 10/2002 | Morgan et al. |
| 2004/0093036 | A1* | 5/2004 | Eckerdal ................ A61N 1/056 607/9 |
| 2005/0070972 | A1 | 3/2005 | Wahlstrand et al. |
| 2006/0184143 | A1 | 8/2006 | Jolly et al. |
| 2007/0123765 | A1 | 5/2007 | Hetke et al. |
| 2008/0027504 | A1* | 1/2008 | Bedenbaugh ........ A61N 1/0529 607/45 |
| 2009/0234426 | A1 | 9/2009 | Pellinen et al. |
| 2011/0015713 | A1 | 1/2011 | Min |
| 2012/0143273 | A1 | 6/2012 | Stubbs et al. |
| 2014/0067023 | A1 | 3/2014 | Register et al. |

OTHER PUBLICATIONS

Paul A. Bottomley, Ananda Kumar, William A. Edelstein, Justin M. Allen and Parag V. Karmarkar. Designing passive MRI-safe implantable conducting leads with electrodes. Med. Phys. 37, 3828 (2010); http://dx.doi.org/10.1118/1.3439590.

William R. Overall, John M. Pauly, Pascal P. Stang, and Greig C. Scott. Ensuring safety of implanted devices under MRI using reversed RF polarization. Magnetic resonance in medicine. vol. 64, Issue 3, Article first published online: Jun. 30, 2010.

Jules M. Nazzaro, Joshua A. Klemp, William M. Brooks, Galen Cook-Wiens, Matthew S. Mayo, Gustat M. Van Acker III , Kelly E. Lyons, and Paul D. Cheney http://informahealthcare.com/doi/abs/10.3109/00207454.2013.840303. Deep brain stimulation lead-contact heating during 3T MRI: single- versus dual-channel pulse generator configurations. Mar. 2014, vol. 124, No. 3, pp. 166-174 (doi:10.3109/00207454.2013.840303).

* cited by examiner

MAGNETIC RESONANT IMAGING SAFE STYLUS

CROSS-REFERENCE TO RELATED APPLICATION

This application is the 35 U.S.C. § 371 national stage of, and claims priority to and the benefit of, PCT application PCT/US2015/026824, filed Apr. 21, 2015, which claims priority to and the benefit of U.S. Application No. 61/981,940, filed on Apr. 21, 2014, the entire contents of each which are hereby incorporated herein by reference.

BACKGROUND

The early diagnosis of diseases can mean the difference between life and death for a patient. To achieve early diagnosis, various non-invasive diagnostic imaging techniques have been developed. X-ray technology, for example, has been utilized since the beginning of the $20^{th}$ century to provide relatively non-invasive diagnostic imaging, but it has limitations, such as when imaging soft tissue. Computed tomography (CT) X-ray technology has elevated the ability to image soft tissue. Further, positron emission tomography (PET) allows the imaging of functional processes in the body. Diagnostic sonography (ultrasonography) uses sound waves to image internal organs and muscle tissue, for example. Diagnostic imaging technique may be categorized according to the quality and specificity of resulting images provided. Most diagnostic imaging techniques create relatively low resolution images, requiring extensive interpretation.

BRIEF DESCRIPTION OF THE DRAWINGS

For a more complete understanding of the embodiments and the advantages thereof, reference is now made to the following description, in conjunction with the accompanying figures briefly described as follows.

The drawings illustrate only example embodiments and are therefore not to be considered limiting of the scope of the embodiments described herein, as other embodiments are within the scope of this disclosure. The elements and features shown in the drawings are not necessarily drawn to scale, emphasis instead being placed upon clearly illustrating the principles of the embodiments. Additionally, certain dimensions or positionings may be exaggerated to help visually convey certain principles. In the drawings, similar reference numerals between figures designate like or corresponding, but not necessarily the same, elements.

DETAILED DESCRIPTION

Magnetic resonance imaging (MRI) exposes a patient to relatively high strength magnetic fields (e.g., 3 Tesla (T) to 7 T or higher) to align the hydrogen (H) atoms dispersed through soft tissue. The MRI then generates powerful alternating electromagnetic (EM) field to pull the aligned H atoms out of position. As they return to their alignment in the alternating EM field, they induce EM signals which are measured and transformed into a detailed image of target tissues. The resolution of the image increases with the power of the magnetic field produced. In a side by side comparison of CT, MRI, PET, CT/PET, and MRI/PET imaging techniques, the MRI and MRI/PET techniques provide greater imaging resolutions.

Many implantable biomedical devices use EM waves to provide therapeutics and sensing capabilities. Two such devices are deep brain stimulation (DBS) devices and heart pacemakers, both of which are examples of biomedical devices which make use of implantable styluses. As electrical devices, they contain conductive materials, most notably metals, to transport signals to or from one or more implanted sites of operation. In that context, one problem is that the electrons which provide electrical transportation in these conductive materials will couple with external EM fields, such as those relied upon in MRI imaging techniques, leading to the induction of eddy currents and standing electrical waves. Thus, it may be dangerous to conduct MRI imaging on patients having DBS or heart pacemaker stylus or probe implants embedded in brain or other tissue.

This issue of magnetic field coupling can be evaluated by examining the underlying EM principals. In metals, the electron conduction and valence bands overlap, providing a ready source of transportable electrons. For insulators, there is a band gap of forbidden energies between the valence and conduction bands that prevents valence electrons from moving into the conduction band. For semiconductors, this band is smaller and can be surmounted with a relatively small application of energy (i.e., a potential bias). Furthermore, dopant impurities can be used to provide electrons (or holes) into the conduction (or valence) bands.

Joule heating is a byproduct of the interaction of induced currents with electrical resistance within a material. The coupling of MRI and associated radio frequency (RF) fields in an implantable electrode based device has been shown to create localized Joule heating, particularly at the end of lead wires where the stylus is located. In strong EM fields, the heating produces an elevation of the local temperature to dangerous levels, potentially leading to irreversible brain damage in human patients. Additionally, the current induced by powerful EM fields in may generate undesirable stimulation effects.

It is noted that Joule heating energy interacts with materials through properties such as thermal conductivity and heat capacity. DBS and pacemaker leads are often constructed from insulators, such as polymers, with the majority of the stylus being composed of conductive materials. In most conductors, thermal conductivity is high, and heat capacity is low, whereas most insulators have low conductivity and high heat capacity. Water has a much higher thermal conductivity than most insulators and has more contact area with the stylus electrodes. This further facilitates the transport of thermal energy into extracellular environments surrounding a probe or stylus implant. The high heat capacity of water is also a contributing factor in the local temperature rise.

For many individuals, finding a solution to the problem of heating in styluses during MRI imaging techniques could increase the likelihood that a physician can correctly diagnose and provide adequate therapeutics for diseases. Additionally, using MRI or other imaging techniques in connection with implantable biomedical devices, it may be possible to more accurately understand the brain and use this knowledge to discover new cures and therapeutics techniques.

According to aspects of the embodiments described herein, silicon carbide (SiC) is relied upon as a material for the construction of a DBS or heart pacemaker stylus, although the concepts may be applied to other types of implantable biomedical devices. Crystalline SiC is a semiconductor material known for its use in the high power and transportation industries due to its wide energy band gap, but it possesses other physical properties that suit it for use in chemical environments. One crystalline substrate, cubic silicon carbide (3C-SiC), shows promise as it can be produced with a considerably reduced cost compared to the commercial hexagonal substrates (6H- and 4H-SiC). However, any crystalline substrate can be utilized in the fabrication of the electrical components of the devices described herein.

Amorphous SiC (a-SiC) may be relied upon in the embodiments as an insulation and hermetic sealing material, a-SiC films deposited by plasma-enhanced chemical vapor deposition (PECVD) on (or on the insulation of) Platinum (PT) and Iridium (Ir) wires may be relied upon to provide good electrochemical stability, a-SiC has also been shown to provide good hemocompatibility when compared with drug eluting stents through clinical testing of a-SiC coated stents in human trials. Polycrystalline SiC can be used as a ceramic material, and has been shown to possess a high degree of biological acceptance, both in vitro and in vivo, and has also demonstrated good levels of hemocompatibility.

Crystalline, amorphous, and polycrystalline SiC may all have a thermal conductivity close to that of copper (i.e., about 3.6 to 4.9 $Wcm^{-1}$° $C.^{-1}$). Additionally, non-conductive, low-doped SiC (amorphous and polycrystalline) with a relative magnetic permeability of 0.999 does not couple with EM fields and, therefore, will not produce additional heat. The designs described herein rely on the high thermal transport but low heat capacity of SiC to provide a thermal pathway which will conduct induced heat throughout a stylus (and into its leads), to dissipate more evenly into the body. The leads may be made thermally conductive, at least in part, by impregnating a-SiC nano-particles into the polymer matrix of the insulation of the leads.

A secondary design issue for DBS and pacemaker styluses, for example, is directed to the determination of an appropriate stimulation target to achieve a suitable level of therapy. It is noted that each disease has a different physiological foundation that includes different signaling pathways as well as different signaling paradigms within these pathways. Contacts in styluses are often greater than 1 mm long or 1 mm in diameter to provide a sufficiently large surface area. Unfortunately, such large surface areas combined with the difficulty of device placement during surgery not only affects the area of the brain near the implant but also elicits responses from proximal neural circuits. The unwanted stimulation and loss of specificity has led many to link DBS to the development of speech impediments, loss of executive functions, and generation of various neuropsychiatric problems.

However, reducing the size of the contacts leads to a problem that has plagued microelectrode cortical implant research. Conductive materials can move charge to and from biological tissue through two processes: Faradaic and non-Faradaic transfer. Faradaic charge transfer is reversible and relies on reduction and oxidation of species present at the surface of the conductive material. Non-faradaic charge transfer depends on charge movement around the double layer. For Faradaic materials, there is a limit to the charge injection before irreversible reactions occur and reactive chemical species are generated which can damage nearby neural tissue. The charge injection limit of 50 to 150 $\mu C/cm^2$ has been measured for Pt/Ir, and for the electrodes listed earlier, there is a limitation of 0.05 to 0.15 $\mu C$ of injection during any phase. Although this value falls within the tissue damage limitation of 30 $\mu C/cm^2$ per phase, dissolution of the electrodes has been observed at a charge injection of 20-50 $\mu C/cm^2$. While this is not a major issue for large DBS electrodes, it can become an issue with smaller area stimulation electrodes. Additionally, a DBS electrode rated at 2000Ω (typical maximum for certain DBS leads) will produce dangerous levels of charge injection for all phases at voltages of 10.5-0.5 V.

As a semiconductor, SiC interacts with the electrolytic environment differently than the pseudo-capacitive Pt/Ir. At lower levels of doping (e.g., <$10^{10}/cm^{-3}$), semiconductors use capacitive transfer using a space charge region. At higher levels of doping (e.g., <$10^{20}/cm^{-3}$), the semiconductor acts as a metal using Faradaic charge transfer. Little research has been performed for high-doped SiC. However, capacitive charge for low-doped nanocrystalline SiC has double-layer capacitance of 30-35 $\mu F/cm^2$, which naturally provides the safe limits of charge transfer without using Faradaic interactions.

In the following paragraphs, the embodiments are described in further detail by way of example with reference to the attached drawings. The embodiments are not to be considered limited in structure, form, function, or application to the examples set forth herein.

Figure 1:
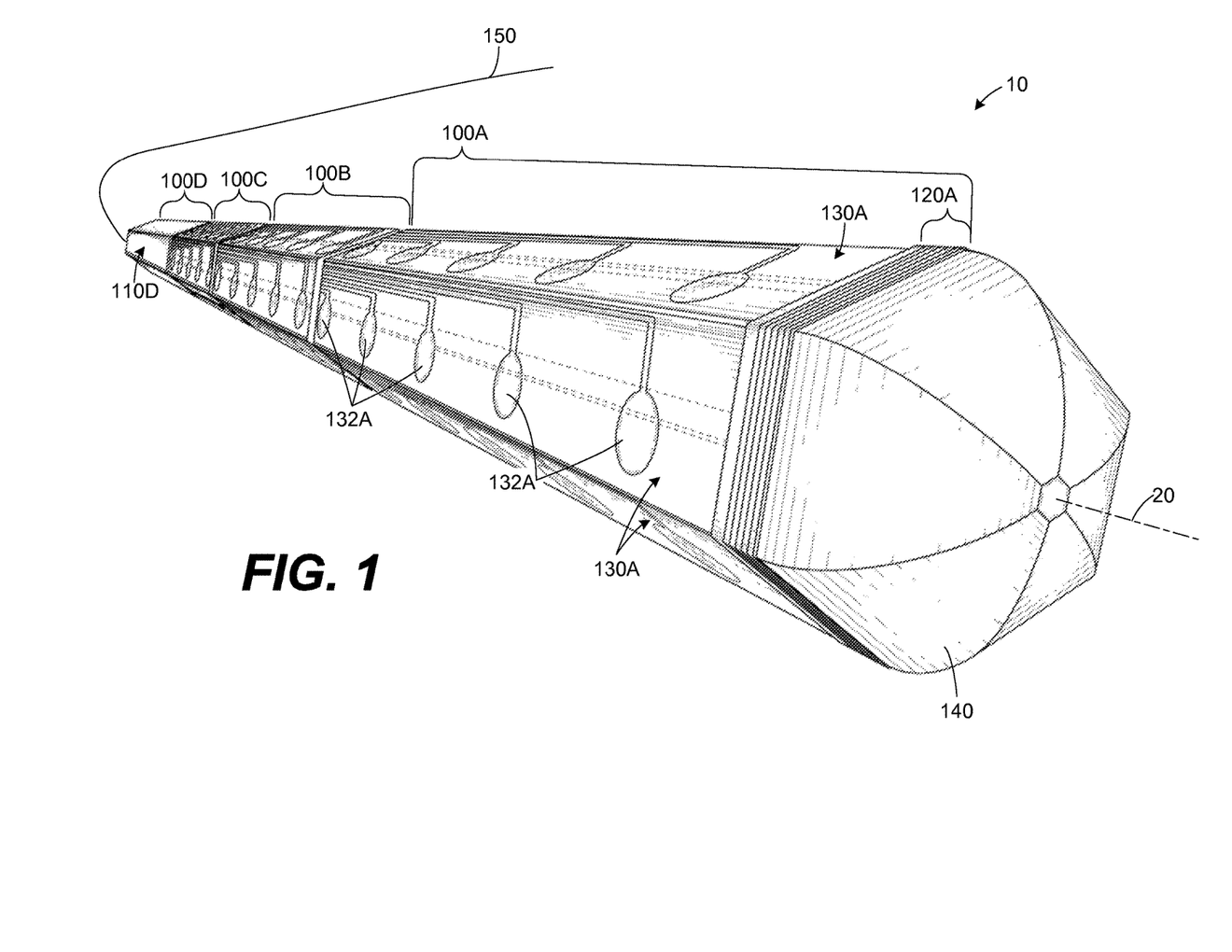
FIG. 1 illustrates a perspective view of a stylus according to an example embodiment described herein.

FIG. 1 illustrates a perspective view of a stylus 10 according to an example embodiment described herein. The stylus 10 is designed to be modular, as described below, to allow it to be assembled for multiple targeting schemes. As such, the stylus 10 includes stylus modules 100A-100D that extend along a longitudinal axis 20. The shape of the stylus 10 in FIG. 1 is provided by way of example only. That is, although the stylus 10 is illustrated as elongated and hexagonal in shape, the concepts described herein may be applied to a stylus having other shapes (e.g., other numbers and/or configurations of sides, rounded, etc.). In one embodiment, the stylus 10 may be approximately 1-2 mm in diameter and approximately 10-15 mm long, although other sizes are within the scope of the embodiments.

As described in further detail below, each of the stylus modules 100A-100D includes a core rod. While the core rod is mostly covered (i.e., out of view) in each of stylus modules 100A-100C, the core rod 110D of the stylus module 100D is exposed. According to aspects of the embodiments, the core rod 110D may be formed from sintered polycrystalline SiC (poly-SiC). The core rod 110D serves as the structural base for the stylus module 100D, and similar core rods serve as structural components for the stylus modules 100A-C.

Among other methods of manufacture, the core rod 110D (and other core rods of the stylus 10) may be mechanically milled from a base of poly-SiC or similar material, using laser milling, or using another suitable technique, to have tracks that serve as insertion points for the recording arrays described below. Further, grooves can be etched in the center of each track to hold lead wires that are electrically contacted to electrodes in the recording arrays. Further, the center of the core rod 110D can be drilled out for the placement of signaling electrode wires. The tracks, grooves, center holes, and other features of the core rod 110D are described in further detail below with reference to FIG. 3.

The stylus 10 further includes one or more recording arrays and one or more stimulation arrays. For example, the stylus module 100A includes at least one stimulation array 120A mounted at a distal end of a core rod of the module 100A and one or more recording arrays 130A mounted on a peripheral surface of the core rod. In the embodiment illustrated in FIG. 1, the recording arrays 130A extend substantially in a direction of the longitudinal axis 20, while the stimulation array 120A extends at least in part perpendicularly to the direction of the longitudinal axis 20. As shown in FIG. 1, each of the recording arrays 130A includes recording electrodes 132A. In FIG. 1, five recording electrodes 132A are shown in each of the recording arrays 130A, although other numbers of recording electrodes may be relied upon. In some embodiments, a first recording array can include a first number of recording electrodes and a second recording array can include a second number of recording electrodes. Additional features of the stimulation array 120A are described in further detail below with reference to FIG. 3.

The stimulation array 120A and the recording arrays 130A can be fabricated using semiconductor quality SiC. Among other ways, the recording arrays 130A can be fabricated using ion implantation or deep reactive ion etching (DRIE) with epitaxial growth provided by chemical vapor deposition (CVD), as described in further detail below with reference to FIGS. 4A-H and 5A-I. In one embodiment, heteroepitaxial growth of 3C-SiC is relied upon on either silicon on or silicon on insulator (SOI) substrates in a low pressure, hot-wall CVD reactor process. The end product is a 20 to 30 μm film of 3C-SiC on Si. SOI substrates provide good substrates for use in this fabrication process. The advantage in this regard is that the top Si substrate can be nanometers in thickness and released with hydrofluoric acid (HF), avoiding the removal of 100-500 μm of Si through DRIE. While 4H- and 6H-SiC substrates are commercially available, the disadvantage in using these substrates is that either the majority of the wafer is DRIE etched away to produce device components or a smart cut process is needed to produce the final products.

As also illustrated in FIG. 1, the stylus 10 includes a hemispherical cap 140 formed of SiC material and positioned proximate to a distal end of the stylus module 100A. The hemispherical cap 104 may be formed in various shapes and sizes among embodiments, while it should be appreciated that the hemispherical cap 104 may be a prominent point of contact with delicate tissues when the stylus 10 is implanted. The stylus 10 also includes leads 150. The leads 150 may include both one or more stimulation leads that extend through a central aperture of the core rods of the stylus 10 and one or more recording leads that extend in the grooves of the core rods. At one end, the leads 150 can be electrically coupled to stimulation and/or recording arrays, such as the stimulation array 120A and the recording arrays 130A. At another end, the leads 150 can be electrically coupled to a DBS, pacemaker, or other diagnostic equipment (not shown).

Figure 2:
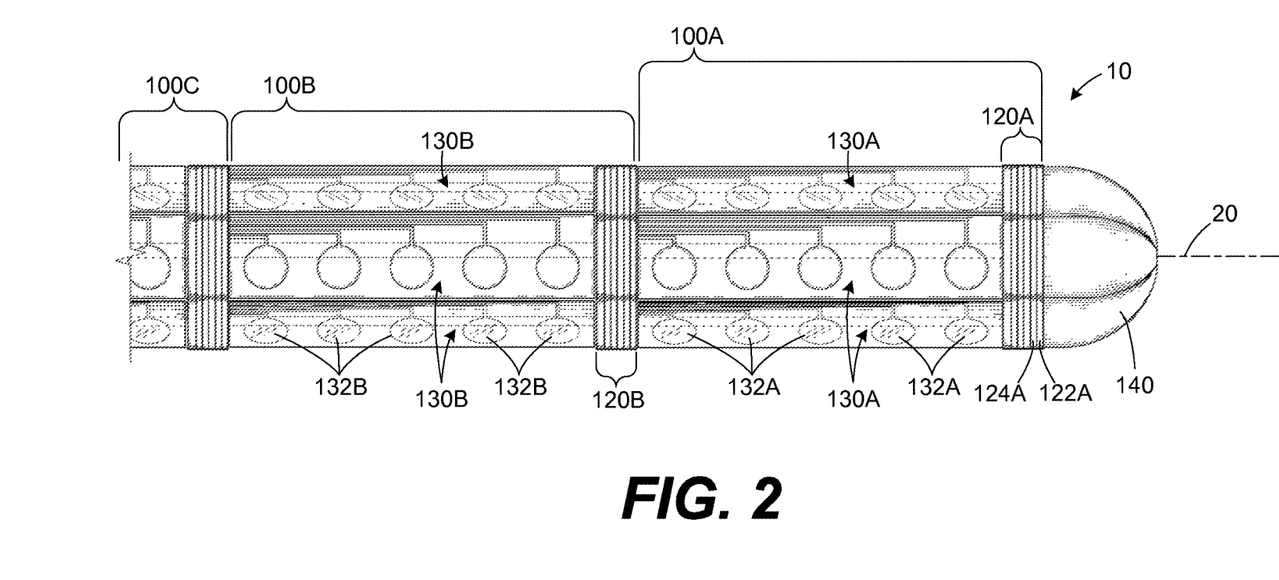
FIG. 2 illustrates a plan view of a portion of the stylus in FIG. 1 according to an example embodiment described herein.

As another view of the stylus 10, FIG. 2 illustrates a plan view of a portion of the stylus 10, including the stylus modules 100A-100C and the hemispherical cap 140. Among FIGS. 1 and 2, similar reference numerals designate like or corresponding elements of the stylus 10. In FIG. 2, the stimulation arrays 120A and 120B are both referenced, along with the alternating, layered stimulation electrodes 122A and insulators 124A of the stimulation array 120A. The stimulation electrodes 122A can be formed from any suitable type of SiC or similar material, among embodiments. The insulators 124A may be formed from any suitable type of insulator material (e.g., poly-SiC), with preference for materials that provide good hemocompatibility.

Figure 3:
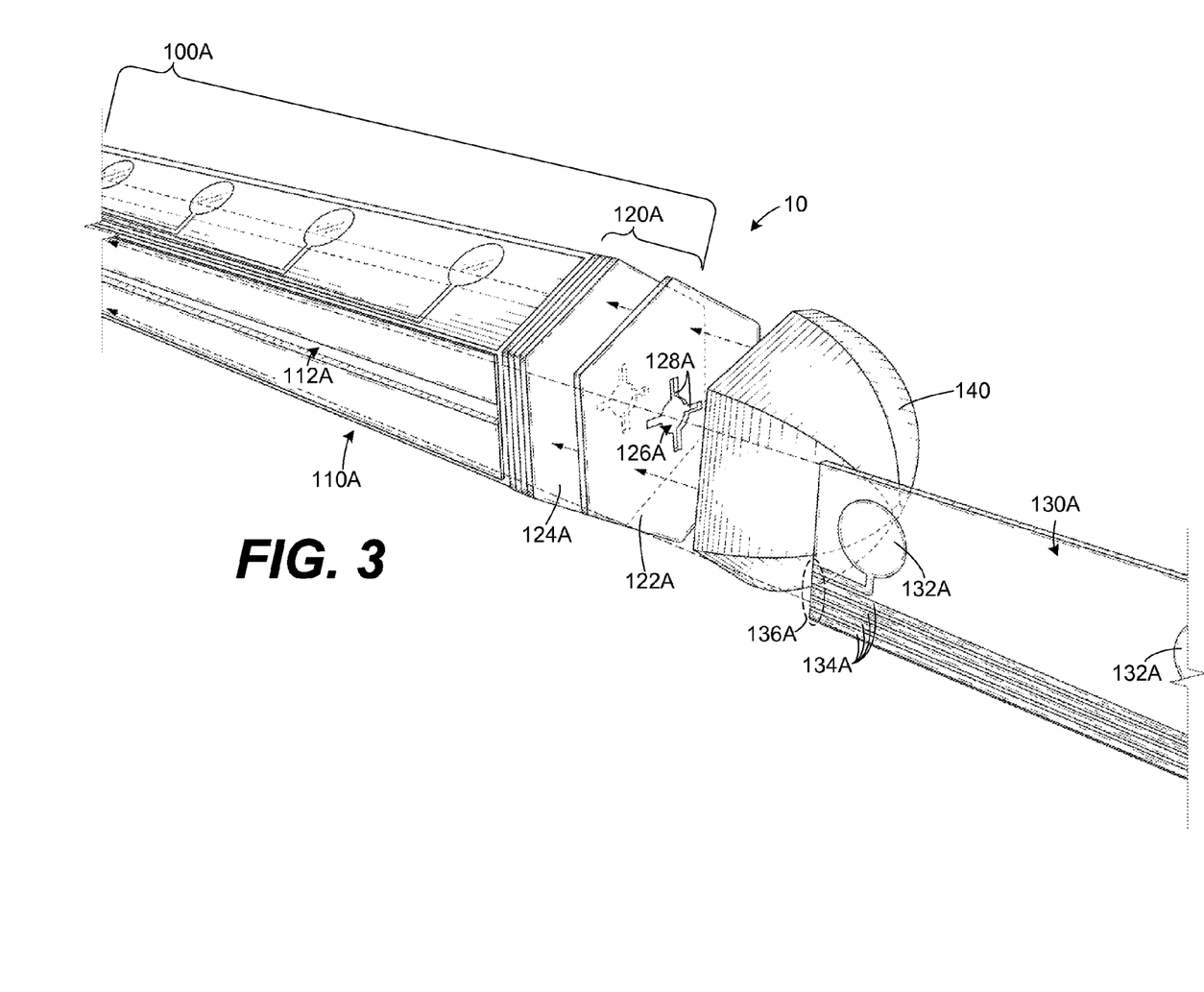
FIG. 3 illustrates an exploded view of a portion of the stylus in FIG. 1 according to an example embodiment described herein.

FIG. 3 illustrates an exploded view of a portion of the stylus 10 according to an example embodiment described herein. Again, among FIGS. 1-3, similar reference numerals designate like or corresponding elements of the stylus 10. In FIG. 3, it is clear that the stimulation array 120A comprises an alternating, layered set of stimulation electrodes 122A and insulators 124A. The stimulation electrodes 122A are nearly circular in shape to avoid electromagnetic edge effects, although other shapes or profiles may be relied upon. It can also be seen that the stimulation electrodes 122A and insulators 124A include a central aperture 126A formed through a center of the stimulation array 120A, and that the central aperture 126A includes peripheral edge notch cutouts 128A. The central aperture 126A in the center of the stimulation array 120A is aligned with the center of the core rod 110A, which can be drilled out for the placement of signaling electrode wires, as described above. The purpose of the peripheral edge notch cutouts 128A is described in further detail below.

The core rod 110A can be milled or cut to include tracks along one or more of its surface edge boundaries, for the insertion of the recording electrode arrays 130A. In that way, the recording electrode arrays 130A may be slid into place as illustrated in FIG. 3. To the extent necessary, adhesives and/or other mechanical means may be relied upon as an additional or alternative means to secure the recording electrode arrays 130A to the core rod 110A.

The core rod 110A of the stylus module 100A is partially exposed in FIG. 3, so that the groove 112A is visible. During assembly, one or more recording leads (e.g., one or more of the leads 150 in FIG. 1) are placed to extend in the groove 112A of the core rod 110A and are electrically coupled to the recording array 130A at one end. As shown in FIG. 3, the recording array 130A includes lead wires or traces 134A, each of which extends to a respective one of the recording electrodes 132A. The lead wires or traces 134A come together at a region of contract pads 136 on the recording array 130A, which may be formed at any suitable location on the recording array 130A. One or more of the recording leads placed in the groove 112A can be electrically coupled at one end to the contract pads 136. The leads may be electrically coupled to the traces 134A using laser soldering or another technique.

It should be appreciated that any leads which are placed in and extend through the groove 112A must be sufficiently fine enough (i.e., small in diameter and/or volume) to fit in the groove 112A. Further, because the stylus modules 100A-100D are positioned in an end-to-end arrangement in the stylus 10 (FIG. 1), any given grove in a core rod of one of the stylus modules 100A-100D may be relied upon to channel lead wires for another one of the stylus modules 100A-100D. As such, the leads which run through the groove 112A may be about 40 gauge in size, for example.

Similarly, any stimulation leads which run through the central aperture 126A and the center of the core rod 110A must be sufficiently fine enough to fit through the center. One or more of the stimulation leads which run through the central aperture 126A and the center of the core rod 110A can be electrically coupled at one end to one or more of the stimulation electrodes 122A of the stimulation array 120A.

In the stylus 10, the stylus modules 100A-100D may be secured together along the longitudinal axis 20 in the end-to-end arrangement (FIG. 1) in any suitable way. In one embodiment, at one end of each of the core rods, rectangular tabs can be milled outside the central hole. These tabs can be longer than the associated stimulation array of the stylus module. Thus, the rectangular tabs can extend through the peripheral edge notch cutouts (e.g., 128A in FIG. 3) of a stimulation array and into mating openings of a core rod of another one of the stylus modules 100A-100D or into the hemispherical cap 140, as a mechanical mating connection. Additionally or alternatively, other mechanical attachments means can be relied upon, such as snap-fit connections, mechanical detents, screws, adhesives, pins, etc.

After the stylus 10 is fully assembled, a-SiC can be used to hermetically seal and fix the entire stylus 10 (excluding the electrode contacts, e.g., 132A, etc.) or any portion thereof. As such, the stylus 10 is hermetically sealed, preventing exposure of the underlying modules and leads to the body and to fixing the assembly into one piece. It is additionally noted that the stimulation and recording leads (e.g., the leads 150 in FIG. 1), which may be embodied as Pt/Ir flouropolymer wires, can be encapsulated within a parylene C insulator. The parylene C insulators can further be impregnated with a-SiC nanoparticles using the techniques described in U.S. patent Ser. No. 13/569,743, filed Aug. 8, 2012, titled "Polypropylene Mesh Impregnated with SiC (Silicon Carbide) Nanoparticles," the entire contents of which are hereby incorporated herein by reference. The stylus 10 may also be sterilized, as necessary, before implantation.

In the following paragraphs, example manufacturing processes of the recording arrays in the stylus 10 are described. At the outset, it is noted that doping profiles for SiC can be generated through the addition of nitrogen or aluminum, for example, to provide electrons or holes, respectively. In situ doping during growth only increases the dopant density to $\sim 10^{18}$ cm$^{-3}$. To increase the conductivity of the material further, ion implantation or another suitable technique may be required. Ion implantation annealing can be performed in argon, when needed, as this process has shown excellent results.

Figure 4A:
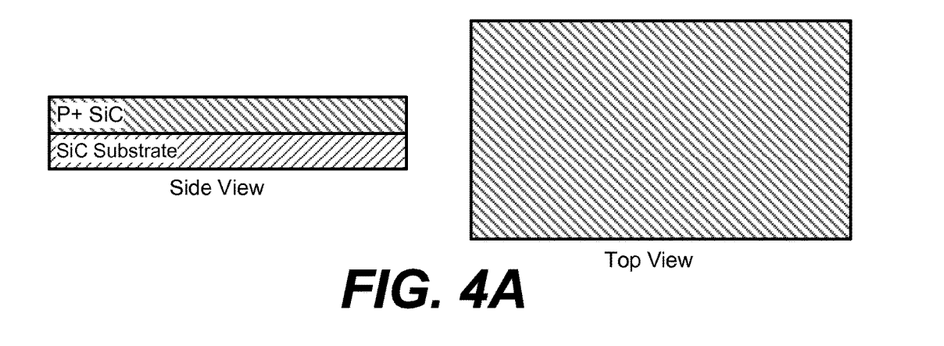
FIGS. 4A-4H illustrate a sequence of states in a first manufacturing process for an electrode used in the stylus in FIG. 1 according to examples of the embodiments described herein.
Figure 4B:
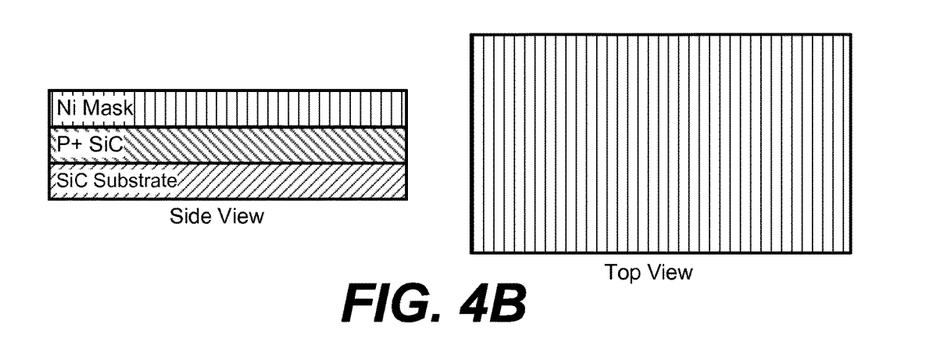
Figure 4C:
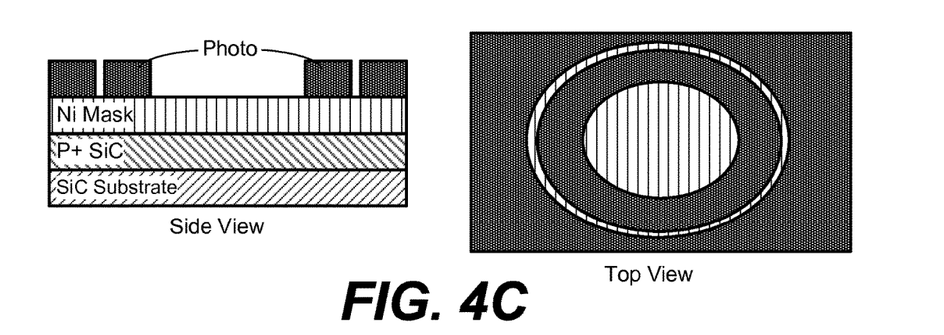
Figures 4D, 4E:
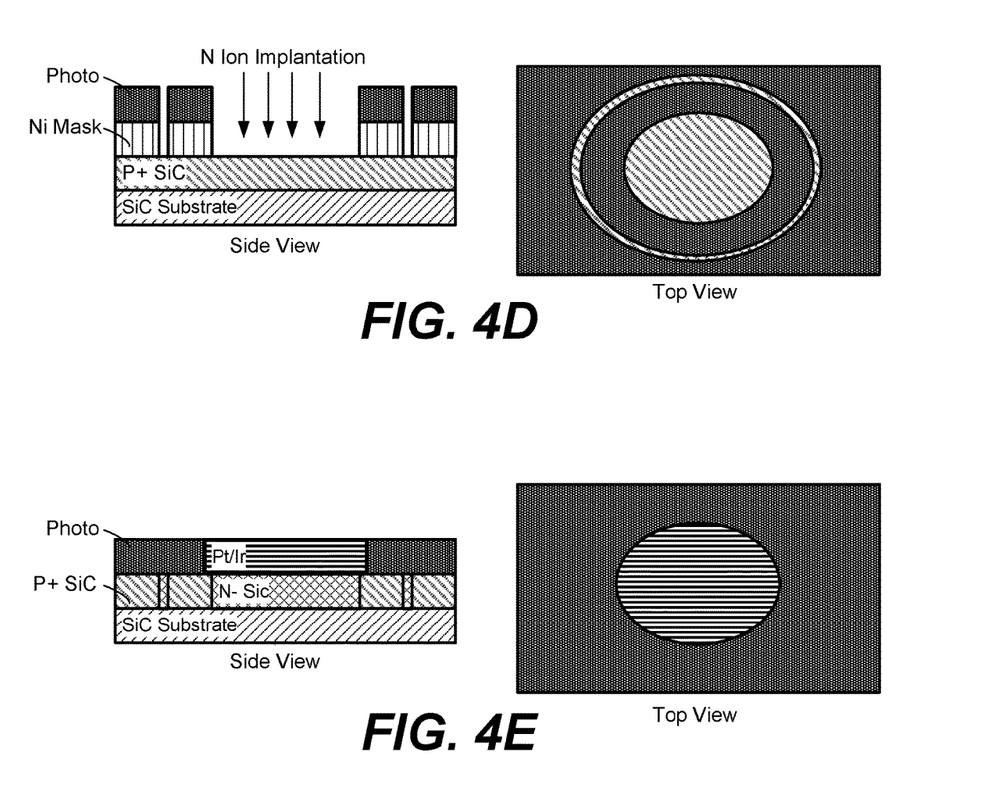

First, an example manufacturing processes flow for the production of SiC electrodes through ion implantation is described with reference to FIGS. 4A-4H. In FIGS. 4A-4H, a side view is shown to the left and a top view is shown to the right. In FIG. 4A, 20-30 µm, for example, of SiC is p-type doped through in situ growth on a SiC substrate. Ion implantation and annealing can be used if high doping density is required for the application. Next, a hard nickel mask is evaporated onto the surface as shown in FIG. 4B. As shown in FIGS. 4C and 4D, photolithography and metal etching of the hard nickel mask are used to define electrode and P-N isolation sites.

Figure 4F:
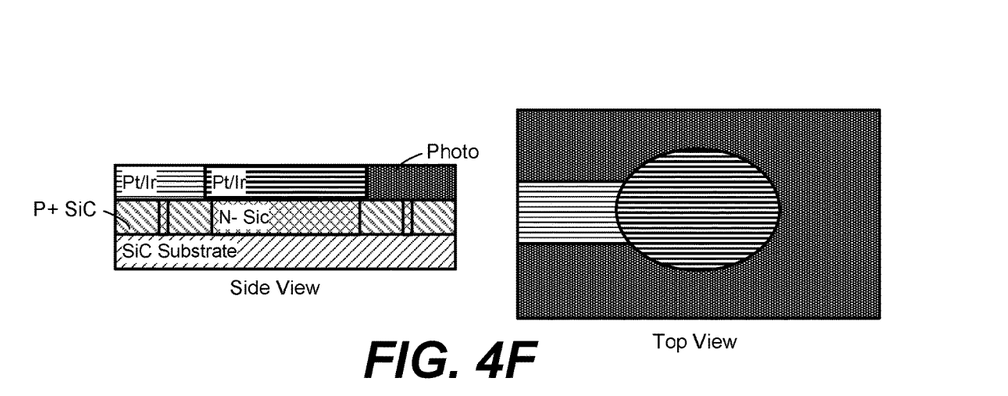
Figure 4G:
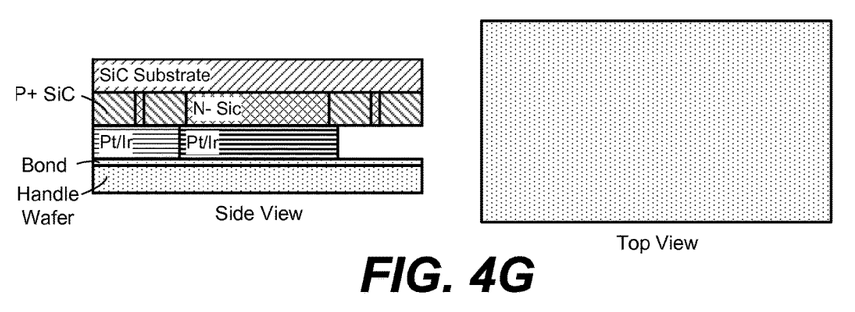
Figure 4H:
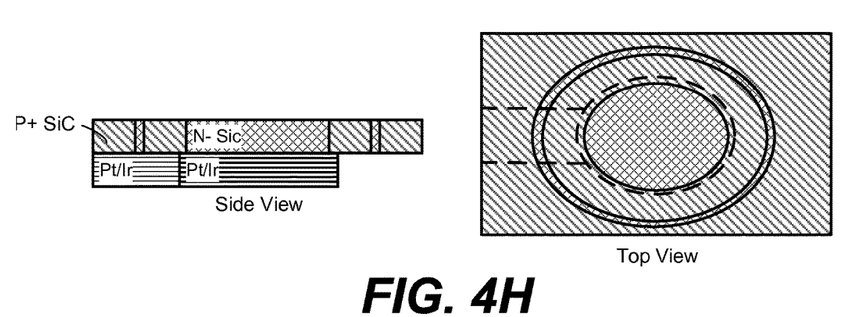

Ion implantation using N ions is performed, as also shown in FIG. 4D, followed by removal of the photo and Ni masks and annealing. In FIG. 4E, photolithography is relied upon to define Pt/Ir backside contacts surrounding the ion-implanted N— SiC regions. In one embodiment, the Pt/Ir backside metal contacts are made ohmic through furnace annealing. Turning to FIG. 4F, photolithography is relied upon to define the Pt/Ir lead or trace wires. In one embodiment, no annealing is performed for the traces, to maintain Schottky diode isolation.

At this stage, for 3C-SiC films on Si (or SiC) wafers, the wafer is flipped and attached onto a handle wafer using a bonding polymer like Crystalbond™. To arrive at the electrode shown in FIG. 4H, for 3C-SiC on SOI, the wafer is HF dipped to release the 3C-SiC film. For a smart cut process, the handle wafer is used and the wafer is mechanically separated. The electrode is then chemically mechanically polished. It is noted that, in the process shown among FIGS. 4A-4H, p- and n-types can be exchanged.

Figure 5A:
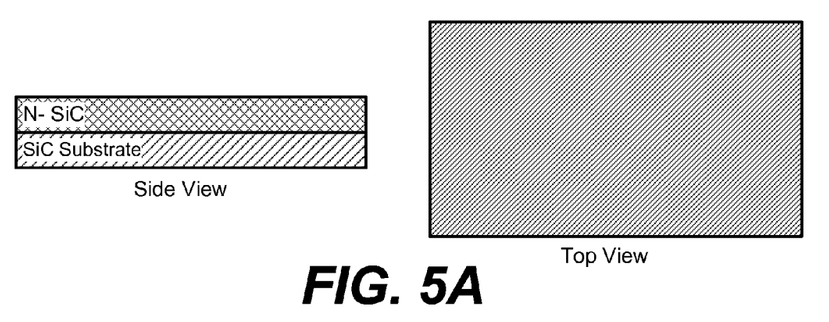
FIGS. 5A-5I illustrate a sequence of states in a second manufacturing process for an electrode used in the stylus in FIG. 1 according to examples of the embodiments described herein.
Figure 5B:
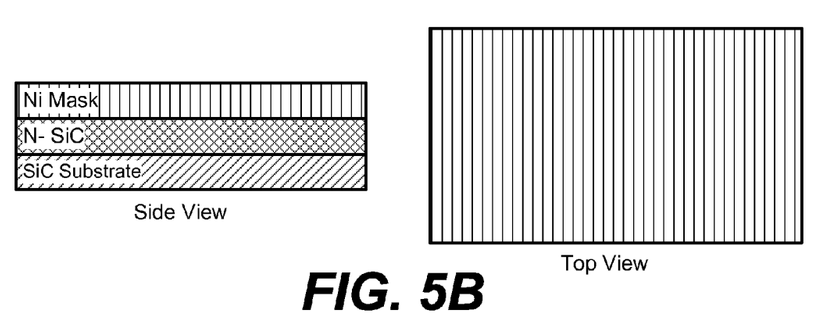
Figure 5C:
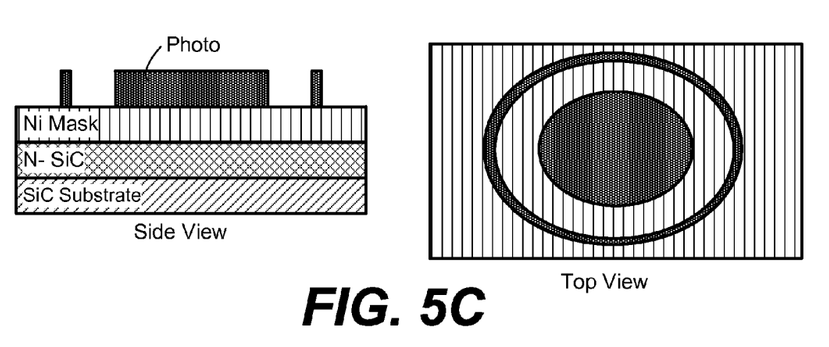
Figure 5D:
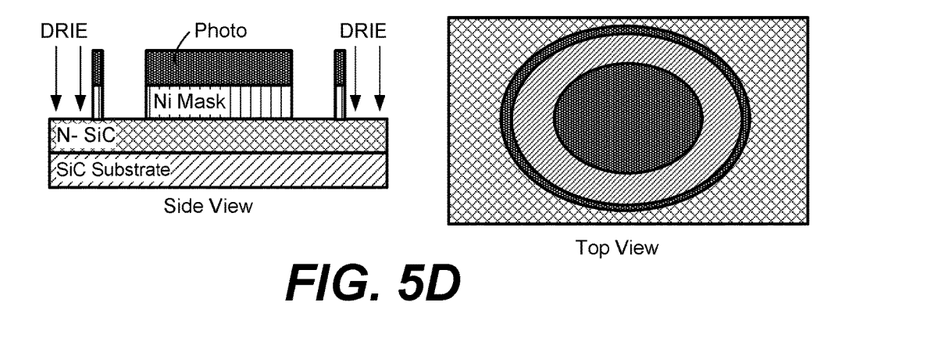
Figure 5E:
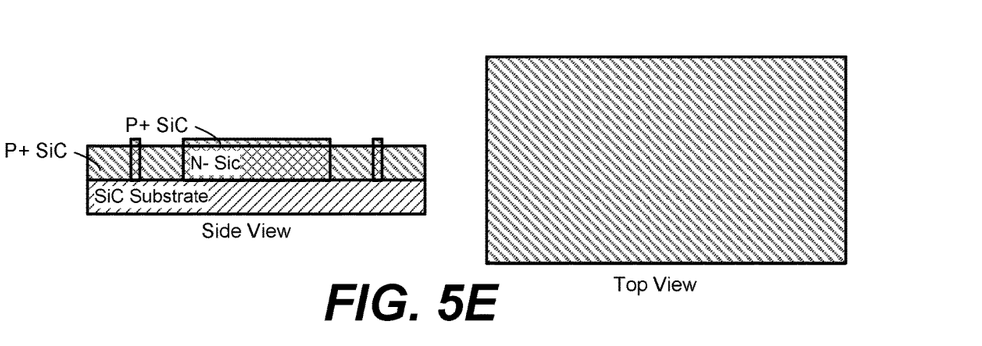

As another example manufacturing processes, a flow for the production of SiC electrodes through epitaxial growth is described with reference to FIGS. 5A-5I. Turning to FIG. 5A, 20-30 µm of SiC, for example, is n-type doped through in situ growth. Ion implantation and annealing can be used if high doping density is required for the application. As shown in FIG. 5B, a hard nickel mask is evaporated onto the surface, and photolithography and metal etching are used to define electrode and P-N isolation sites, as shown among in FIGS. 5C and 5D. As further shown in FIG. 5D, DRIE is used to etch the epitaxial layer of SiC to the substrate to define the electrode contacts. In FIG. 5E, epitaxial growth of p-type SiC is grown over the SiC electrodes. Chemical-mechanical planarization (CMP) polishing is used to planarize the electrode and expose the electrode contacts.

Figure 5F:
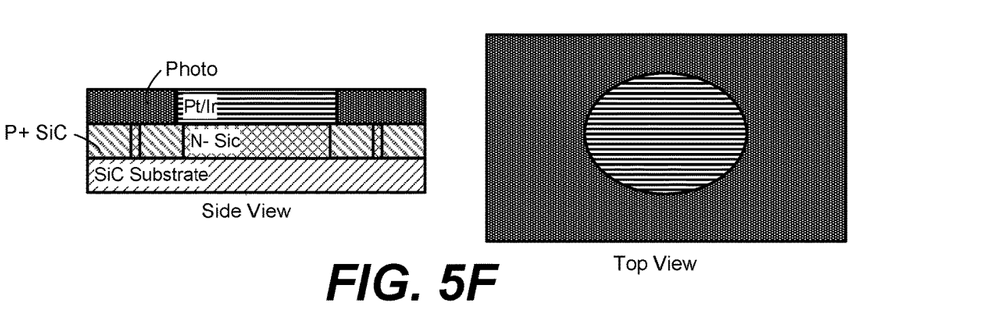
Figure 5G:
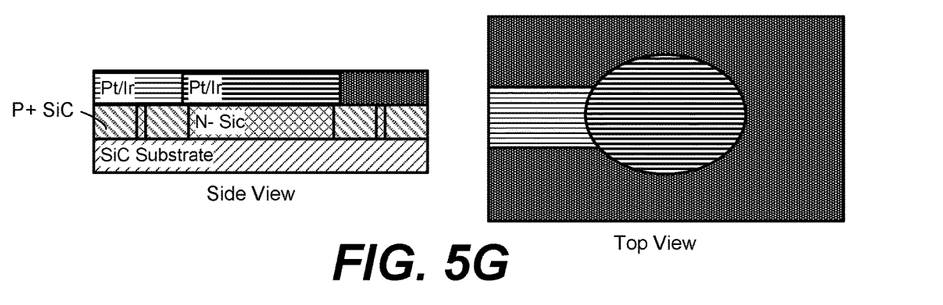
Figure 5H:
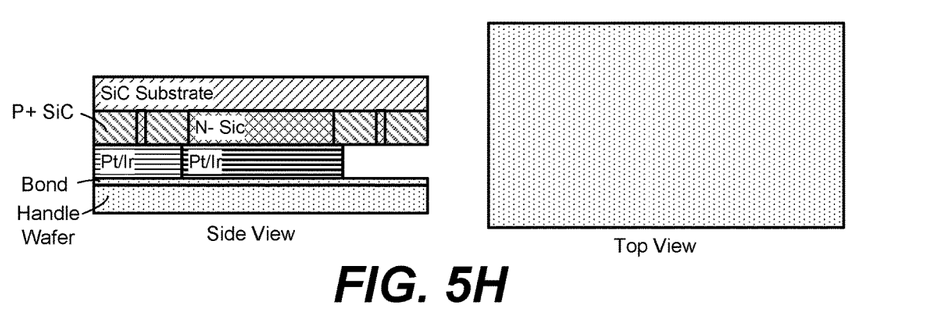
Figure 5I:
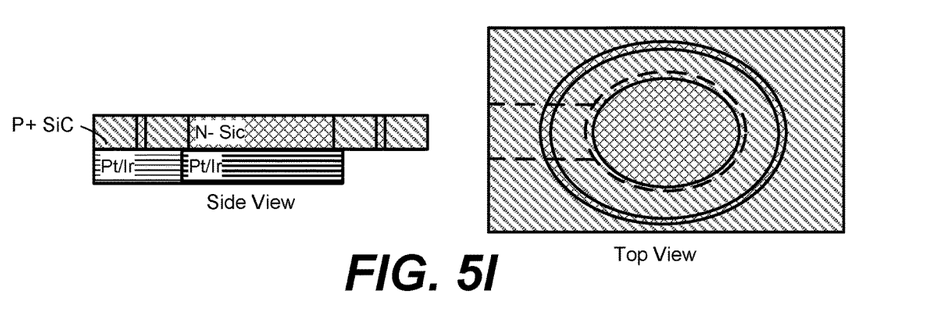

In FIG. 5F, photolithography is relied upon to define the Pt/Ir backside contacts. The metal contacts can be made ohmic through furnace annealing. Further, as can be seen in FIG. 5G, photolithography can be relied upon to define the Pt/Ir lead wires. No annealing is performed to maintain Schottky diode isolation.

At this stage, for 3C-SiC films on Si (or SiC) wafers, the wafer is flipped and attached onto a handle wafer using a bonding polymer like Crystalbond™. To arrive at the electrode shown in FIG. 4H, for 3C-SiC on SOI, the wafer is HF dipped to release the 3C-SiC film. For a smart cut process, the handle wafer is used and the wafer is mechanically separated. The electrode is then chemically mechanically polished. It is noted that, in the process shown among FIGS. 5A-5I, p- and n-types can be exchanged. Also, the contacts which will connect the electrodes to the Pt/Ir transport wires (e.g., the leads 150 in FIG. 1) can be created using e-beam evaporation, followed by photolithographic patterning and metal etching.

Both of the processes shown in FIGS. 4A-4H and 5A-5I can produce the multi-electrode recording arrays which can be slid down and/or secured to the core rods of the stylus 10 in FIGS. 1-3, and the signaling arrays can be constructed in a similar manner.

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present invention defined in the following claims, the scope of which are to be accorded the broadest interpretation so as to encompass modifications and equivalent structures.

What is claimed is:
1. A stylus, comprising:
  a plurality of stylus modules, at least one of the plurality of stylus modules comprising:
    a core rod formed of silicon carbide (SiC) material that extends a distance along a longitudinal axis of the core rod;

a recording array mounted on at least a portion of a peripheral surface of the core rod that extends substantially in a direction of the longitudinal axis of the core rod, the recording array comprising at least one electrode formed through ion implantation of a doped substrate of SiC material; and a stimulation array mounted at a distal end of the core rod, the stimulation array including at least one stimulation electrode that extends at least in part perpendicularly to the direction of the longitudinal axis of the core rod;

a hemispherical cap formed of SiC material positioned proximate to a distal end of one of the plurality of stylus modules; and a hermetic seal that seals the plurality of stylus modules from exposure to body tissue.

2. The stylus of claim 1, wherein the core rod comprises:
a groove in the peripheral surface of the core rod that extends substantially in the direction of the longitudinal axis; and
a central aperture that extends through a center of the core rod substantially in the direction of the longitudinal axis.

3. The stylus of claim 2, further comprising:
a stimulation lead that extends through the central aperture of the core rod and is electrically coupled to the stimulation array at one distal end; and
a recording lead that extends in the groove of the core rod and is electrically coupled to the recording array at one distal end.

4. The stylus of claim 3, wherein an insulator of at least one of the stimulation lead and the recording lead is impregnated with SiC nanoparticles.

5. The stylus of claim 3, wherein:
the stimulation array includes a central aperture formed through a center of the stimulation array, the central aperture including peripheral edge notch cutouts;
the stimulation lead extends to the central aperture of the stimulation array and is electrically coupled to the stimulation array at the central aperture; and
the core rod includes tabs which extend through the peripheral edge notch cutouts of the stimulation array and mechanically mate into the hemispherical cap.

6. The stylus of claim 1, wherein:
the recording array comprises a plurality of recording electrodes; and
each of the plurality of recording electrodes comprises an electrode and associated isolation ring formed through ion implantation of a doped substrate of SiC material.

7. The stylus of claim 6, wherein the recording array further comprises a planar metal contact and planar lead trace for each of the plurality of recording electrodes.

8. The stylus of claim 1, wherein the hermetic seal is formed from a coating of amorphous SiC deposited using chemical vapor deposition.

9. A stylus module, comprising:
a core rod formed of silicon carbide (SiC) material that extends a distance along a longitudinal axis of the core rod;
a recording array comprising a plurality of recording electrodes mounted on at least a portion of a peripheral surface of the core rod, wherein each of the plurality of recording electrodes comprises an electrode formed through ion implantation of a doped substrate of SiC material and respectively extend substantially in a direction of a longitudinal axis of the core rod;

a stimulation array mounted at a distal end of the core rod; and a hermetic seal that seals the core rod and recording array from exposure to body tissue.

10. The stylus module of claim 9, wherein the core rod comprises:
a groove in a peripheral surface of the core rod that extends substantially in a direction of the longitudinal axis; and
a central aperture that extends through a center of the core rod substantially in the direction of the longitudinal axis.

11. The stylus module of claim 10, further comprising:
a stimulation lead that extends through the central aperture of the core rod and is electrically coupled to the stimulation array at one distal end; and
a recording lead that extends in the groove of the core rod and is electrically coupled to the recording array at one distal end.

12. The stylus module of claim 11, wherein an insulator of at least one of the stimulation lead and the recording lead is impregnated with SiC nanoparticles.

13. The stylus module of claim 11, wherein:
the stimulation array includes a central aperture formed through a center of the stimulation array, the central aperture including peripheral edge notch cutouts; and
the stimulation lead extends to the central aperture of the stimulation array and is electrically coupled to the stimulation array at the central aperture.

14. The stylus module of claim 9, wherein the recording array further comprises a planar metal contact and planar lead trace for each of the plurality of recording electrodes.

15. The stylus module of claim 9, wherein the hermetic seal is formed from a coating of amorphous SiC deposited using chemical vapor deposition.

16. The stylus module of claim 9, further comprising a hemispherical cap formed of SiC material positioned proximate to a distal end of the core rod.

17. A stylus, comprising:
a plurality of stylus modules, at least one of the plurality of stylus modules comprising:
a core rod formed of silicon carbide (SiC) material that extends a distance along a longitudinal axis of the core rod;
a recording array comprising a plurality of recording electrodes mounted on at least a portion of a peripheral surface of the core rod, wherein each of the plurality of recording electrodes comprises an electrode formed through ion implantation of a doped substrate of SiC material; and
a stimulation array formed of SiC material, the stimulation array including at least one stimulation electrode;
a hemispherical cap formed of SiC material positioned proximate to a distal end of one of the plurality of stylus modules; and
a hermetic seal that seals the plurality of stylus modules from exposure to body tissue.

18. The stylus of claim 17, further comprising:
a stimulation lead that is electrically coupled to the stimulation array; and
a recording lead that is electrically coupled to the recording array, wherein an insulator of at least one of the stimulation lead and the recording lead is impregnated with SiC nanoparticles.

19. The stylus of claim 18, wherein:
the stimulation array includes a central aperture formed through a center of the stimulation array; and
the stimulation lead extends to the central aperture of the stimulation array and is electrically coupled to the stimulation array at the central aperture.

20. The stylus of claim 18, wherein the hermetic seal is formed from a coating of amorphous SiC deposited using chemical vapor deposition.

\* \* \* \* \*